United States Patent [19]
Bennett, Jr.

[11] 4,415,086
[45] Nov. 15, 1983

[54] INOCULUM TRAY

[76] Inventor: John T. Bennett, Jr., P.O. Box 155, 21131 Georgia Ave., Brookeville, Md. 20833

[21] Appl. No.: 472,369

[22] Filed: Mar. 4, 1983

[51] Int. Cl.³ .......................... B65D 1/34; B65D 6/04
[52] U.S. Cl. ..................................................... 206/564
[58] Field of Search ............... 206/557, 558, 564, 565, 206/370, 363; 229/2.5 R

[56] References Cited

U.S. PATENT DOCUMENTS

| | | | |
|---|---|---|---|
| 3,357,625 | 12/1967 | Malmgren | 229/2.5 |
| 3,591,032 | 7/1971 | Baxter | 206/564 |
| 3,697,223 | 10/1972 | Kovalcik et al. | 206/370 |
| 4,153,160 | 5/1979 | Leigh | 206/564 |
| 4,354,601 | 10/1982 | Harrison | 206/564 |

Primary Examiner—Joseph Man-Fu Moy
Attorney, Agent, or Firm—Sughrue, Mion, Zinn, Macpeak and Seas

[57] ABSTRACT

A substantially rectangular inoculum tray is provided with a reservoir in the upper surface thereof having at least one apertured side wall with the bottom surface of each aperture being at least at the level of the bottom surface of the reservoir. A plurality of parallel identical grooves are formed in the upper surface of the tray with one end of each groove being in communication with a respective aperture. The bottom surface of each groove is disposed below the bottom surface of the reservoir so that upon introducing a liquid medium into said reservoir a pressure head will be formed so that a uniform distribution of the liquid will occur from the reservoir into each individual groove.

3 Claims, 6 Drawing Figures

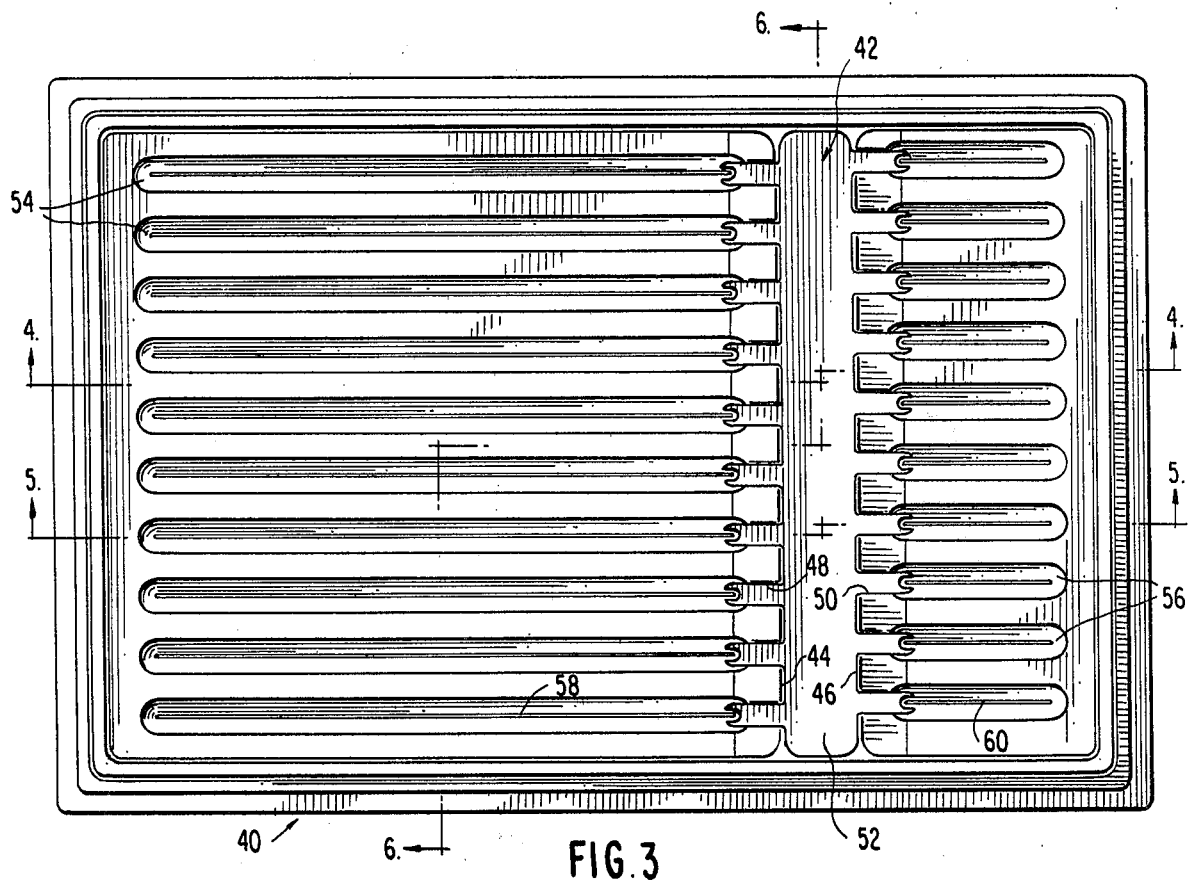
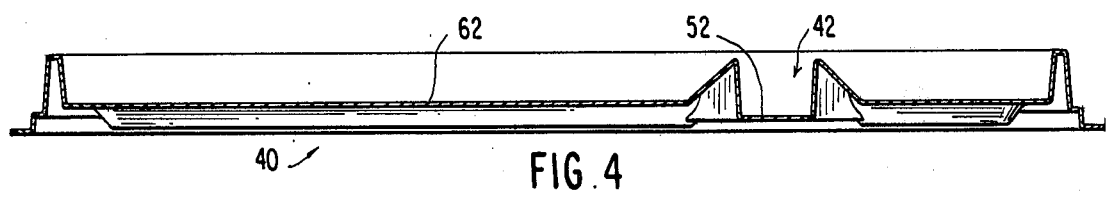
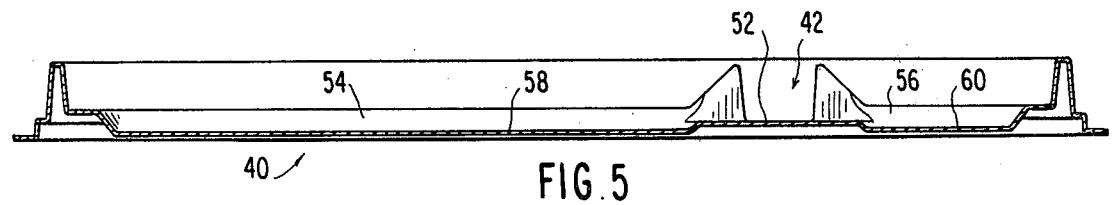
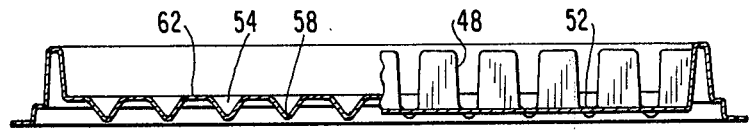

INOCULUM TRAY

BACKGROUND OF THE INVENTION

The present invention is directed to an inoculum tray and more specifically to a tray having a plurality of grooves connected to a common reservoir through control orifices to facilitate uniform distribution of a test reagent from the reservoir to the individual grooves with sufficient concentration to facilitate pick up of the reagent by pipettes or the like.

With conventional transfer dishes such as a generally flat shallow petri dish it has always been a problem of achieving uniform distribution of the liquid reagent due to the nonwetting characteristic of the plastic used in their manufacture and the surface tension effect of the reagent. In order to achieve uniform distribution it was often necessary to rock the dish back and forth which could present a dangerous handling situation depending upon the nature of the reagent.

In addition to the problem of non-uniform distribution, the use of shallow, flat bottom dishes also created a transfer problem when it was necessary to transfer the liquid reagent by means of pipettes or the like from a flat bottom dish to a multi-well test plate as a micro-titer plate. Due to the shallow depth of the liquid reagent, it was difficult to achieve a uniform pick-up of the liquid reagent by means of a multi-tube pipette device.

In order to overcome the foregoing disadvantages it has been proposed to provide one or more depressions in the bottom of a dish at the point of pick-up or to provide a plurality of inter-connected troughs to minimize waste surface area. However, the problem of even distribution to the recesses or troughs still created a problem.

SUMMARY OF THE INVENTION

The present invention provides a new and improved inoculum tray which overcomes the afore-mentioned problems associated with the use of flat bottom, shallow dishes in a simple, economical manner.

The present invention provides a new and improved inoculum tray comprising a reservoir having a bottom surface and a side wall provided with a plurality of orifices extending therethrough flush with the bottom surface of said reservoir and a plurality of elongated grooves each of which is disposed in fluid communication with a respective orifice with the bottom of each groove having a depth greater than the bottom of said reservoir.

The foregoing and other objects, features and advantages will be apparent from the following more particular description of a preferred embodiment of the invention as illustrated in the accompanying drawings.

BRIEF DESCRIPTION OF THE DRAWINGS

FIG. 3 is a top-plan view of a modified form of an inoculum tray according to the present invention.

FIG. 4 is a sectional view taken along the line 4—4 of FIG. 3.

FIG. 5 is a sectional view taken along the line 5—5 in FIG. 3.

FIG. 6 is a sectional view taken along the line 6—6 in FIG. 3.

DETAILED DESCRIPTION OF THE INVENTION

Figure 1:
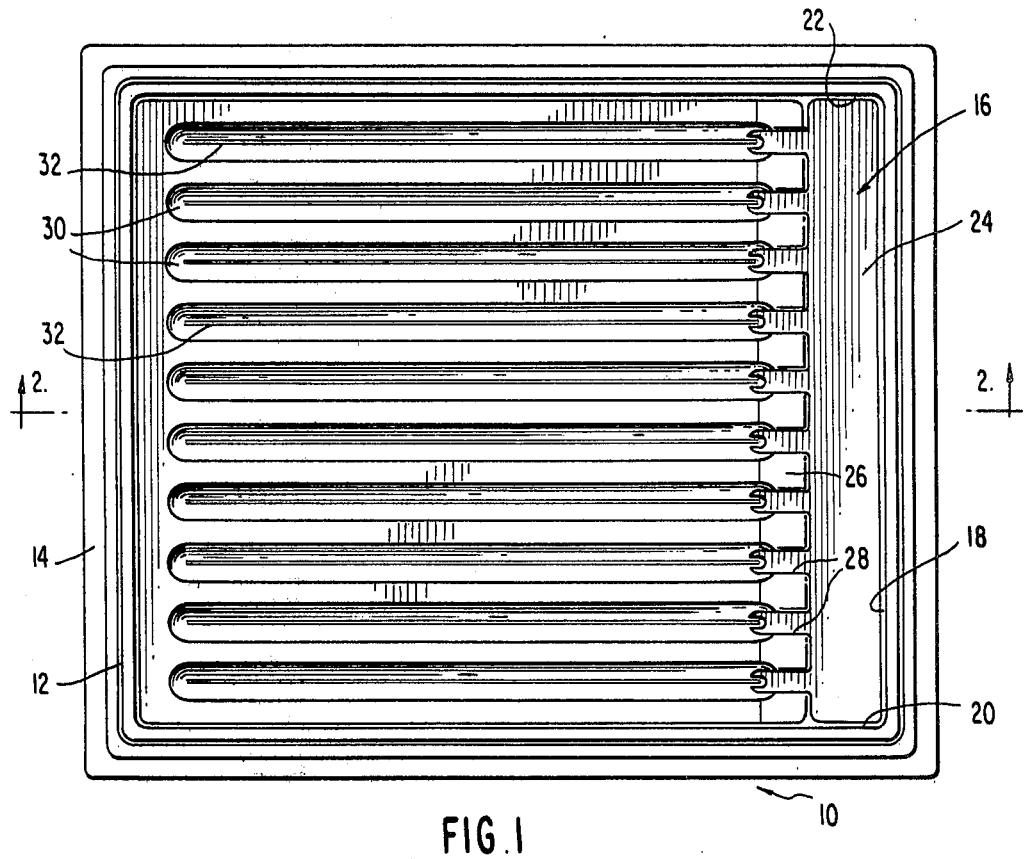
FIG. 1 is a top plan view of an inoculum tray according to the present invention.

In the embodiment of the invention as shown in FIG. 1, the inoculum tray 10 is comprised of a one-piece molded tray of plastics material or the like. The tray is provided with an inwardly tapered outer side wall 12 extending about the entire periphery of the tray and a laterally extending support flange 14. The tapered side wall permits the stacking a plurality of trays to facilitate storage of the trays in a convenient manner. A reservoir 16 is defined along one side of the tray 10 by means of a first elongated side wall 18 extending substantially the entire length of the side of the tray, a pair of short end walls 20 and 22, a bottom wall 24, and a second elongated side wall 26, equal in length to the side wall 18, but having a plurality of relatively narrow apertures 28 extending therethrough with the bottom of each aperture being flush with the bottom wall 24 of the reservoir 16.

Figure 2:
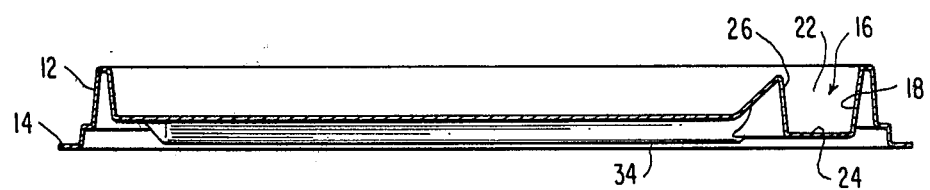
FIG. 2 is a cross-sectional view taken along the line 2—2 of FIG. 1.

A plurality of parallel, identical, elongated grooves 30 are formed in the upper surface of the tray with one end of each groove being disposed in communication with a respective aperture 28. The bottom surface 32 of each groove is located below the bottom surface 24 of the reservoir. This is best seen in FIG. 2 wherein the bottom outer surface 34 of the groove 30 is illustrated below the bottom surface 24 of the reservoir 16.

Thus, in using the inoculum tray according to the present invention, the entire pre-determined amount of a liquid medium is poured directly into the reservoir 16. Due to the restrictive size of the apertures 28 the flow of liquid from the reservoir will be restricted so that a pressure head will be created within the reservoir 16. This pressure head will therefore cause a completely uniform distribution of the liquid medium into each of the grooves 30 so that each groove 30 will have an identical volume of the liquid medium therein. Due to the configuration of the grooves 30 the liquid medium within each groove will have a sufficient depth to allow an accurate, uniform pick-up of the liquid medium from each groove by means of a pipette device or the like.

A modified form of the inoculum tray is shown in FIG. 3 wherein the tray 40 is provided with a reservoir 42 extending the entire width of the tray. Each of the longer side walls 44 and 46 of the reservoir 42 are provided with identical apertures 48 and 50, respectively, each of which has a bottom surface flush with the bottom surface 52 of the reservoir 42. A first plurality of elongated grooves 54 are formed in the upper surface of the tray 40 with one end thereof in communication with a respective orifice 48. A second set of elongated grooves 56 are also formed in the upper surface of the tray 40 with one end thereof in communication with the apertures 50. The bottom surfaces 58 of the grooves 54 and the bottom surfaces 60 of the grooves 56 are all disposed below the bottom surface 52 of the reservoir 42, as best seen in FIG. 5. As in the previous embodiment upper surface 62 of the tray is disposed at a level higher than the bottom surface 52 of the reservoir 42.

While the inoculum tray may be vacuum formed as illustrated in the foregoing embodiment, it is also conceivable that the tray could be injection molded, machined, or formed by any other suitable process. Likewise, while the various grooves have been shown parallel to each other and perpendicular to the reservoir, it is also conceivable that the reservoir could be formed as a cylindrical recess having an apertured side wall with the various grooves radiating outwardly therefrom. The dimensions of the apertures can vary depending upon the amount and physical characteristics of the liquid medium being used.

While the invention has been shown and described with reference to preferred embodiments thereof, it will be understood by those in the art that the foregoing and other changes in form and detail may be made therein without departing from the spirit and scope of the invention.

What is claimed is:

1. A liquid handling tray having an upper surface, a reservoir formed in the upper surface of said tray with a bottom surface spaced below said upper surface and a side wall having a plurality of apertures therein with the bottom of each aperture being at least at the level of the bottom surface of said reservoir and a plurality of grooves formed in the upper surface of said tray with the bottom surface thereof being disposed below the bottom surface of said reservoir whereby the liquid poured into said reservoir will be uniformly distributed through said apertures into said grooves.

2. A liquid handling tray as set forth in claim 1 wherein said tray has a rectilinear configuration with said reservoir extending substantially the entire width of said tray perpendicular to the side edges thereof and said grooves are disposed parallel to each other perpendicular to said reservoir.

3. A liquid handling tray as set forth in claim 2 further comprising a second set of parallel grooves extending perpendicular to said reservoir on the opposite side thereof from said first mentioned grooves, said reservoir having a second apertured side wall with the bottom of each aperture being disposed at least at the level of the bottom surface of said reservoir and each of said second set of grooves having a bottom surface below the bottom surface of said reservoir.

* * * * *